US008388558B2

(12) United States Patent
Matsuoka et al.

(10) Patent No.: US 8,388,558 B2
(45) **Date of Patent: *Mar. 5, 2013**

(54) WALKING ASSISTANCE DEVICE

(75) Inventors: Yoshihisa Matsuoka, Tochigi (JP); Yutaka Hiki, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 798 days.

This patent is subject to a terminal disclaimer.

(21) Appl. No.: 12/575,827

(22) Filed: Oct. 8, 2009

(65) Prior Publication Data

US 2010/0113988 A1 May 6, 2010

(30) Foreign Application Priority Data

Nov. 5, 2008 (JP) ................................ 2008-284819

(51) Int. Cl.
*A61H 1/00* (2006.01)
*A61H 1/02* (2006.01)
*A61F 5/052* (2006.01)

(52) U.S. Cl. .................. 601/5; 601/35; 602/16; 602/23

(58) Field of Classification Search ................ 601/5, 23, 601/26, 27, 33, 34, 35; 602/5, 16, 23, 26, 602/27; 482/51, 66, 74–79; 135/65, 67
See application file for complete search history.

(56) References Cited

U.S. PATENT DOCUMENTS

| | | | | |
|---|---|---|---|---|
| 5,129,273 | A * | 7/1992 | Fukui et al. | 74/89.35 |
| 5,189,927 | A * | 3/1993 | Egan | 74/602 |
| 5,547,464 | A * | 8/1996 | Luttrell et al. | 602/26 |
| 6,676,707 | B2 * | 1/2004 | Yih et al. | 623/24 |
| 2006/0270951 | A1 * | 11/2006 | Ikeuchi | 601/5 |

FOREIGN PATENT DOCUMENTS

| | | |
|---|---|---|
| JP | 02-019660 | 1/1990 |
| JP | 10-034714 | 2/1998 |
| JP | 2002-191654 | 7/2002 |
| JP | 2002-523687 | 7/2002 |
| JP | 2006-043871 | 2/2006 |
| JP | 2008-012224 | 1/2008 |
| WO | 00/10775 | 3/2000 |

* cited by examiner

*Primary Examiner* — Justine Yu
*Assistant Examiner* — Valerie L Skorupa
(74) *Attorney, Agent, or Firm* — Rankin, Hill & Clark LLP

(57) ABSTRACT

A walking assistance device has a drive mechanism, which is provided with a linear-motion actuator including an electric motor installed in the upper link member, nut members which are rotationally driven by the electric motor, and a linear-motion output shaft which linearly moves in the direction of the axial centers of the nut members, and a crank arm which is secured to the lower link member coaxially with a joint axis of a third joint and swingably attached to one end of the linear-motion output shaft. The drive mechanism is constructed such that a translational force output from the linear-motion output shaft of the linear-motion actuator is converted into a rotational driving force of the third joint through the crank arm.

7 Claims, 4 Drawing Sheets

WALKING ASSISTANCE DEVICE

BACKGROUND OF THE INVENTION

1. Field of the Invention

The present invention relates to a walking assistance device which assists a user (person) with walking.

2. Description of the Related Art

Hitherto, as this type of walking assistance device, Japanese Patent Application Laid-Open No. 2002-191654 (hereinafter referred to as "patent document 1"), for example, discloses walking assistance equipment constituted of a thigh attachable member to be attached to a thigh and a crus attachable member which is rotatably installed to the thigh attachable member and which is to be attached to a crus. The walking assistance equipment has a drive mechanism comprised of a motor installed to the thigh attachable member, a socket installed to the crus attachable member, a ball screw threaded in a screw hole of the socket, and a flexible joint connecting a motor shaft and the ball screw. The ball screw moves into or out of the socket to change the distance between the bottom end of the flexible joint and the socket, thereby bending the crus attachable member relative to the thigh attachable member. This arrangement enables a walking-impaired person to rotationally move a knee joint and to secure stable gaits.

However, the walking assistance equipment disclosed in patent document 1 has been posing a problem of poor durability, low rotational accuracy, delayed following attributable to the flexible joint used with the drive mechanism. There has been another problem in that the crus attachable member is bent relative to the thigh attachable member by the ball screw moving into or out of the socket, so that the ball screw inevitably has a long stroke, making the ball screw long.

SUMMARY OF THE INVENTION

In view of the problems described above, an object of the present invention is to provide a walking assistance device which is outstanding in durability, rotational movement accuracy, and following capability.

To this end, the present invention provides a walking assistance device including a load transmit assembly which transfers a load for supporting a part of the weight of a user to the body trunk of the user; a foot-worn assembly to be attached to a foot of the user; a leg link which connects the foot-worn assembly to the load transmit assembly, the leg link comprising an upper link member extended from the load transmit assembly via a first joint, a lower link member extended from the foot-worn assembly via a second joint, and a third joint which bendably connects the upper link member and the lower link member; and a drive mechanism for driving the third joint, wherein the drive mechanism has a linear-motion actuator including an electric motor mounted on the upper link member, a nut member which is rotationally driven by the electric motor and disposed in an enclosure swingably supported by the upper link member, and a linear-motion output shaft having a thread groove formed in an outer peripheral surface thereof, the thread groove screwing with the nut member through the intermediary of a ball retained in the nut member, and a crank arm which is secured to the lower link member coaxially with a joint axis of the third joint and swingably attached to one end of the linear-motion output shaft, and the drive mechanism is constructed such that a translational force output from the linear-motion output shaft of the linear-motion actuator is converted into a rotational driving force of the third joint through the crank arm.

According to the present invention, the drive mechanism uses a crank arm, instead of the flexible joint as in the walking assistance device described in the aforesaid patent document 1. Therefore, the drive mechanism of the walking assistance device has better durability, higher rotational movement accuracy, and higher following capability than the walking assistance equipment described in patent document 1. Furthermore, the linear-motion output shaft (ball screw) moves forward and backward to circularly move the crank arm secured to the lower link member coaxially with the joint axis of the third joint, so that a rotational driving force is imparted to the third joint by the drive mechanism. Thus, compared with the walking assistance equipment described in patent document 1 described above, the stroke of the linear-motion output shaft can be shortened, allowing the linear-motion output shaft to be shorter.

When the nut member rotates, the linear-motion output shaft moves in the direction of the axial center thereof, causing a force in the direction of the axial center thereof (thrust force) to act on the nut member. Hence, the nut member has to be supported by a pair of angular bearings. In this case, however, disposing a bearing for swingably supporting an enclosure on the upper link member outside an outer collar interposed between outer rings of the angular bearings would inconveniently increase the width of the linear-motion actuator in the direction of a swinging axis.

In the present invention, therefore, it is desirable to provide a pair of angular bearings which support the nut member by the enclosure such that the angular bearings are spaced apart in the direction of the axis line of the nut member, a pair of opposing openings having an axis line orthogonal to the axis line of the nut member is formed in the outer collar provided between the outer rings of the angular bearings, and the bearing which is positioned in each of the openings and attached to the enclosure is supported by a support shaft protrusively provided on the upper link member. This makes it possible to restrain an increase of the width of the linear-motion actuator in the direction of the swing axis.

Further, in the present invention, the load transmit assembly is composed of a seating member on which a user sits astride. The first joint is preferably provided with an arcuate guide rail, which is connected to the seating member and which extends in a longitudinal direction and which has the center of curvature thereof at above the seating member, and a slider which is secured to an upper end of the upper link member and which movably engages the guide rail.

This arrangement obviates the need for securing a motional space for a connecting link between the linear-motion actuator and the guide rail and allows the position of the linear-motion actuator, i.e., the position of the center of gravity of the linear-motion actuator, to be closer to the guide rail. Furthermore, a force for supporting the weight of a user, that is, the force in the direction for reducing the bending angle of the third joint, is transferred by the pulling of the connecting link. Hence, unlike the case where the force is transferred by pushing, there is no need to increase the section of the connecting link in order to prevent buckling, thus permitting a reduction in the weight of the connecting link itself. As a result, the inertial moment of a leg link around the first joint can be reduced.

In the present invention, the output shaft of the electric motor is preferably provided in parallel to the axis line of the nut member.

With this arrangement, in comparison with, for example, the case where an electric motor is provided orthogonally to the axis line of the nut member, it is possible to restrain the upper link member from projecting in the direction of the width of the linear-motion actuator, considering the external configuration of a typical electric motor. Furthermore, the electric motor is closer to the guide rail, thus permitting a reduction in the inertial moment of the leg link around the first joint. In addition, the rotational driving force of the electric motor can be transferred to the nut member through the intermediary of a simple rotation transferring mechanism composed of a pulley and a belt, allowing the linear-motion actuator to be simplified, smaller and lighter-weight.

Further, the nut member preferably functions as an inner collar interposed between the inner rings of the pair of angular bearings.

This arrangement allows the linear-motion actuator to be simplified, smaller in diameter, and lighter-weight, as compared with the case where the inner collar interposed between the inner rings of the angular bearings is provided separately from the nut member.

DESCRIPTION OF THE PREFERRED EMBODIMENTS

The following will describe a walking assistance device A according to an embodiment of the present invention with reference to the accompanying drawings.

Figure 1:
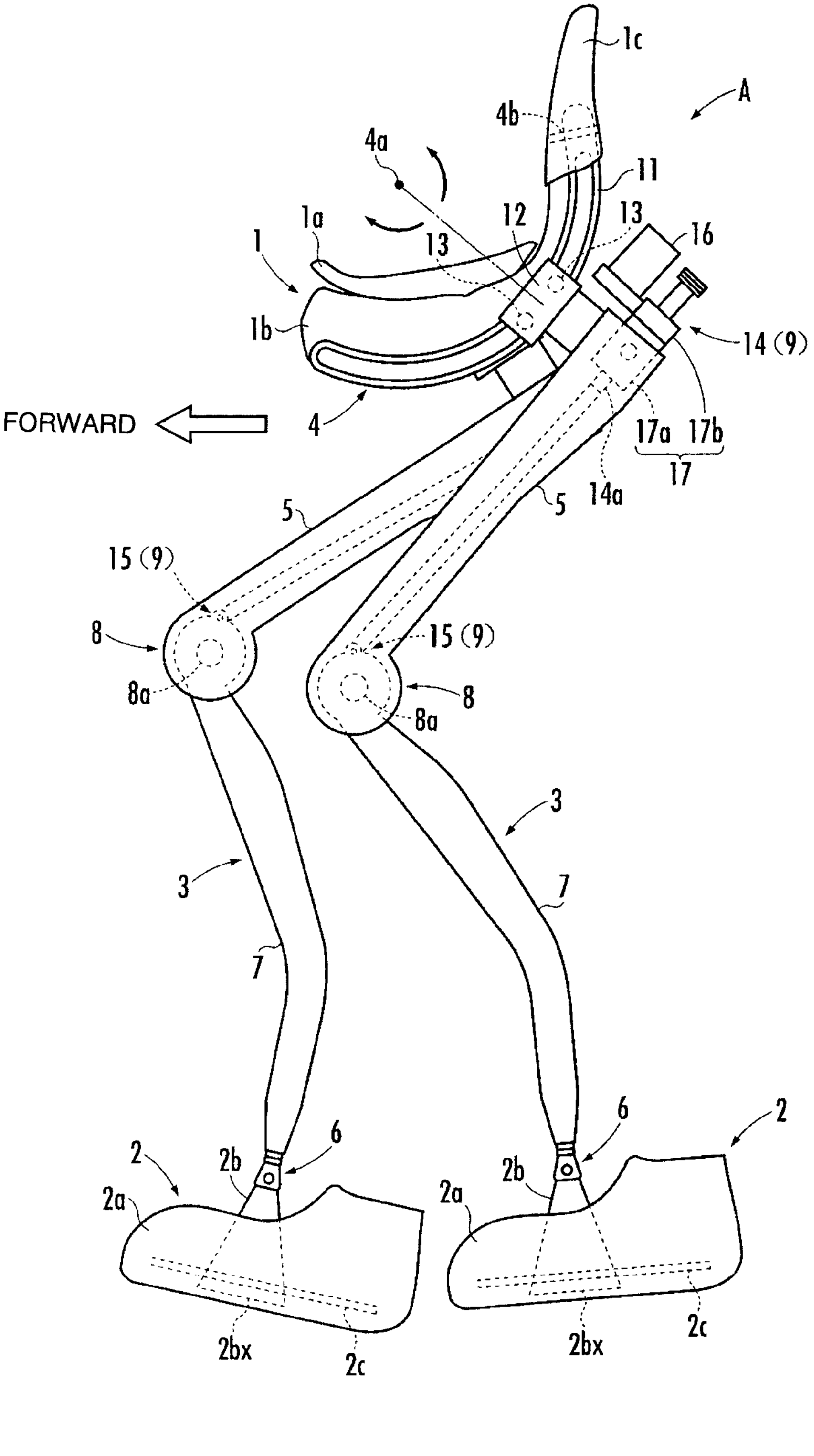
FIG. 1 is a side view illustrating a schematic construction of a walking assistance device according to an embodiment of the present invention.

As illustrated in FIG. 1, the walking assistance device A is provided with a seating assembly 1 serving as a load transmit assembly, a pair of right and left foot-worn assemblies 2 and 2 to be attached to the feet of individual legs of a user (not shown), and a pair of right and left leg links 3 and 3 which connect the foot-worn assemblies 2 and 2, respectively, to the seating assembly 1. The right and left foot-worn assemblies are laterally symmetrical to each other and share the same structure. The right and left leg links 3 and 3 are also laterally symmetrical to each other and share the same structure. In the description of the present embodiment, the lateral direction of the walking assistance device A means the lateral direction of the user having the foot-worn assemblies 2 and 2 attached to his or her feet (the direction substantially perpendicular to the paper surface in FIG. 1).

Each of the leg links 3 is constituted of an upper link member 5 extended downward from the seating assembly 1 via a first joint 4, a lower link member 7 extended upward from the foot-worn assembly 2 via a second joint 6, and a third joint 8 which bendably connects the upper link member 5 and the lower link member 7 between the first joint 4 and the second joint 6.

Further, the walking assistance device A has a drive mechanism 9 for driving the third joint 8 for each leg link 3. The drive mechanism 9 of the left leg link 3 and the drive mechanism 9 of the right leg link 3 are laterally symmetrical and share the same structure. Regarding the drive mechanism 9 of the right leg link 3, a part of the drive mechanism 9 in FIG. 1 is omitted for easy understanding of the illustration.

The seating assembly 1 is constituted of a saddle-shaped seat 1*a* disposed such that the seat 1*a* is positioned between the proximal ends of the two legs of a user when the user sits thereon astride, a base frame 1*b* attached to the bottom surface of the seat 1*a*, and a hip pad 1*c* attached to the rear end portion of the base frame 1*b*, i.e., the portion that rises upward at the rear of the seat 1*a*.

The first joint 4 of each of the leg links 3 is a joint which has a freedom degree (2 degrees of freedom) of rotation about two joint axes, namely, in the longitudinal direction and the lateral direction. More specifically, each of the first joints 4 has an arcuate guide rail 11 attached to the base frame 1*b* of the seating assembly 1. A slider 12, which is secured to the upper end of the upper link member 5 of each of the leg links 3, movably engages the guide rail 11 through the intermediary of a plurality of rollers 13 rotatably attached to the slider 12. This arrangement enables each of the leg links 3 to effect a swing motion in the longitudinal direction (a longitudinal swing-out motion) about the axis of the first joint, taking the lateral axis passing a curvature center 4*a* of the guide rail 11 (more specifically, the axis in the direction perpendicular to a plane that includes the arc of the guide rail 11) as a first joint axis of the first joint 4.

Further, the guide rail 11 is rotatably supported at the rear upper end of the base frame 1*b* of the seating assembly 1 through the intermediary of a support shaft 4*b* having the axial center thereof oriented in the longitudinal direction, so that the guide rail 11 is allowed to swing about the axial center of the support shaft 4*b*. This arrangement enables each of the leg links 3 to effect a lateral swing motion (adduction/abduction motion) about a second joint axis of the first joint 4, taking the axial center of the support shaft 4*b* as the second joint axis of the first joint 4. In the present embodiment, the second joint axis of the first joint 4 provides a joint axis common to the right first joint 4 and the left first joint 4.

As described above, the first joint 4 is constructed to allow each of the leg links 3 to effect swing motions about the two joint axes, namely, in the longitudinal direction and the lateral direction.

The degree of the rotational freedom of the first joint is not limited to two. Alternatively, the first joint may be constructed to have, for example, a freedom degree of rotation about three joint axes, i.e., three degrees of freedom. Further alternatively, the first joint may be constructed to have, for example, a freedom degree of rotation about only one joint axis in the lateral direction, i.e., one degree of freedom.

Each of the foot-worn assemblies 2 has a shoe 2*a* for the user to wear on a foot and a connecting member 2*b* projecting upward from inside the shoe 2*a*. Each leg of the user lands on the ground through the shoe 2*a* in a state wherein the leg is a standing leg, i.e., a supporting leg. The lower end of the lower link member 7 of each of the leg links 3 is connected to the connecting member 2*b* via the second joint 6. In this case, the connecting member 2*b* has, as an integral part thereof, a flat-plate-like portion 2*bx* disposed under an insole 2*c* in the shoe 2*a* (between the bottom of the shoe 2*a* and the insole 2*c*). The connecting member 2*b*, including the flat-plate-like portion 2*bx*, is formed of a member having relatively high rigidity such that, when the foot-worn assembly 2 is landed, a part of a floor reaction force acting from a floor onto the foot-worn assembly 2 (a translational force which is large enough to support the weight combining at least the walking assistance device A and a part of the weight of the user) can be applied to the leg link 3 through the intermediary of the connecting member 2*b* and the second joint 6. The foot-worn assembly 2 may have, for example, slipper-like footwear in place of the shoe 2*a*.

The second joint 6 in the present embodiment is constituted of a free joint, such as a ball joint, and has a freedom degree of rotation about three axes. However, the second joint may alternatively be a joint having a freedom degree of rotation about, for example, two axes in the longitudinal and lateral directions or two axes in the vertical and lateral directions.

The third joint 8 is a joint having a freedom degree of rotation about one axis in the lateral direction and has a support shaft 8*a* rotatably supporting the upper end of the lower link member 7 to the lower end of the upper link member 5. The axial center of the support shaft 8*a* is substantially parallel to the first joint axis of the first joint 4 (the axis in a direction perpendicular to a plane which includes the arc of the guide rail 11). The axial center of the support shaft 8*a* provides the joint axis of the third joint 8, and the lower link member 7 can be relatively rotated about the joint axis with respect to the upper link member 5. This allows the leg link 3 to stretch or bend at the third joint 8.

In order to apply a load for supporting a part of the weight of the user sitting on the seating assembly 1 (an upward translational force) to the user from the seating assembly 1, each of the drive mechanisms 9 imparts a rotational driving force (torque) in the direction in which the leg link 3 stretches to the third joint 8 of the leg link 3 having the foot-worn assembly 2 thereof in contact with the ground. The drive mechanism 9 is mounted on the upper link member 5 of the leg link 3 and constituted of a linear-motion actuator 14 having a linear-motion output shaft 14*a* and a motive power transferring mechanism 15 which converts motive power output from the linear-motion output shaft 14*a*, i.e., a translational force in the axial direction of the linear-motion output shaft 14*a*, into a rotational driving force and imparts the rotational driving force to the third joint 8.

Figure 2:
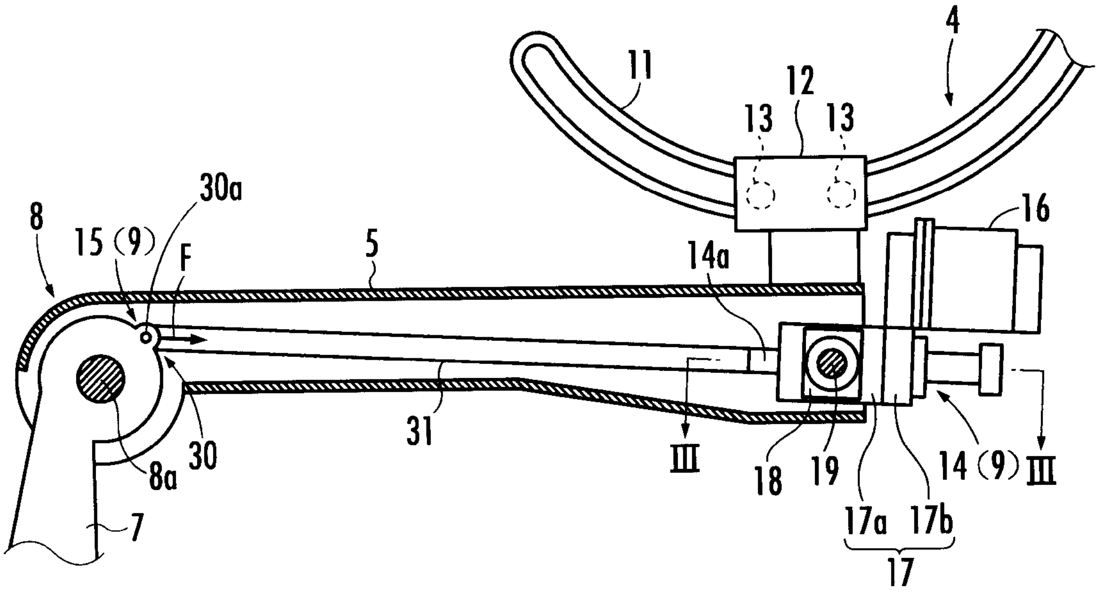
FIG. 2 is a diagram illustrating an upper link member of the walking assistance device in FIG. 1, the upper link member having been partly broken away.
Figure 3:
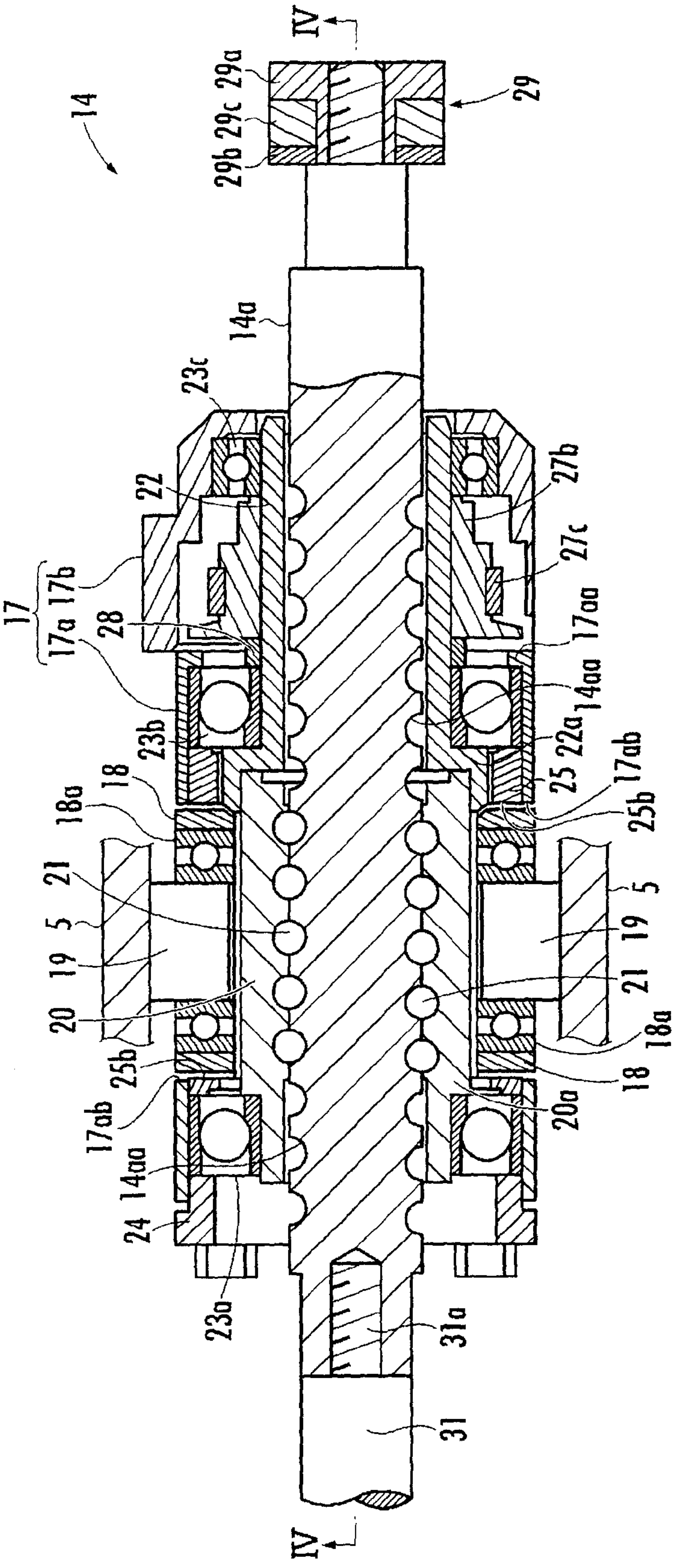
FIG. 3 is a sectional view taken at line in FIG. 2.
Figure 4:
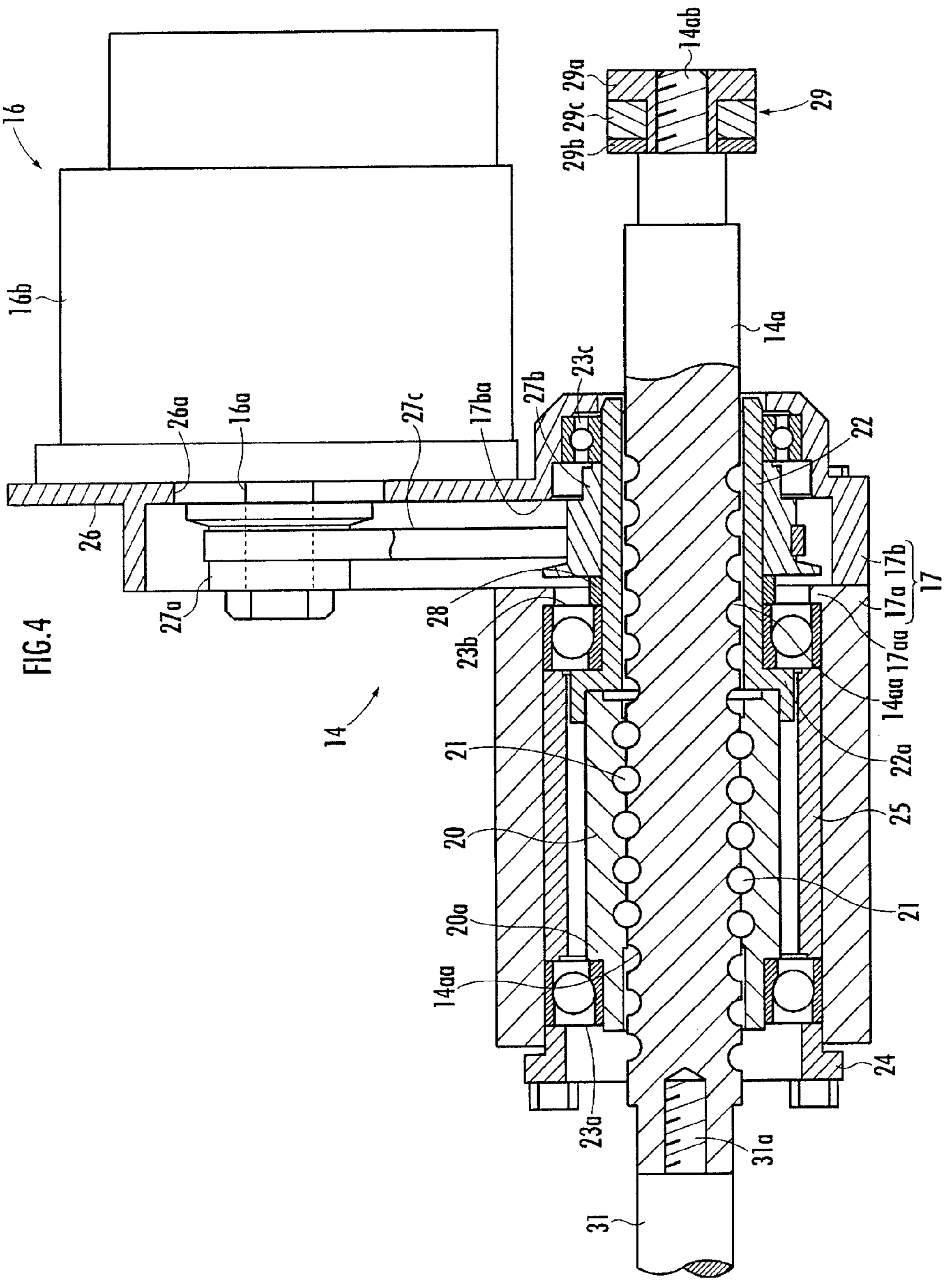
FIG. 4 is a sectional view taken at line IV-IV in FIG. 3.

The following will describe the details of the drive mechanism 9 with reference to FIG. 2 to FIG. 4.

The upper link member 5 to which the drive mechanism 9 is installed has a hollow structure which is open at the end thereof adjacent to the first joint 4 (hereinafter referred to as "the end at the hip side") and at the end thereof adjacent to the third joint 8 (hereinafter referred to as "the end at the knee side), as illustrated in FIG. 2. The linear-motion actuator 14 is disposed at a location on the upper link member 5 adjacent to the end at the hip side, while the motive power transferring mechanism 15 is accommodated in the upper link member 5, extending from the location adjacent to the end at the hip side of the upper link member 5 to the location adjacent to the end at the knee side.

The linear-motion actuator 14 has an electric motor 16 serving as a rotary actuator and an enclosure 17 accommodating mainly a ball screw mechanism for converting a rotational driving force (torque) output from the electric motor 16 into a translational force in the direction of the axial center of the linear-motion output shaft 14*a*. In this case, the enclosure 17 is composed of a main enclosure 17*a*, which has an approximately square-tubular shape, and a hollow subsidiary enclosure 17*b* secured to one end of the main enclosure 17*a*, a linear-motion output shaft 14*a* penetrating the main enclosure 17*a* and the subsidiary enclosure 17*b*. The enclosure 17 is disposed adjacently to the end at the hip side of the upper link member 5 such that the main enclosure 17*a* and the subsidiary enclosure 17*b* are positioned on the inner side and the outer side, respectively, of the upper link member 5, and the axial center of the linear-motion output shaft 14*a* is approximately oriented in the lengthwise direction of the upper link member 5.

As illustrated in FIG. 3, a pair of bearing members 18 and 18 respectively incorporating bearings 18*a* is installed on both sides of the main enclosure 17*a* in the direction orthogonal to the axial center of the linear-motion output shaft 14*a* (the direction substantially perpendicular to the paper surface of FIG. 2). These bearing members 18 and 18 are secured to the main enclosure 17*a* such that the respective bearings 18*a* thereof coaxially oppose.

A support shaft 19, which is protrusively provided such that the support shaft 19 has an axial center parallel to the joint axis of the third joint 8, is fitted from the inner wall of the upper link member 5 into the inner ring of the bearing 18*a* of each of the bearing member 18. With this arrangement, the enclosure 17 is supported by the upper link member 5 such that the enclosure 17 swings about the axial center of the support shaft 19. Hereinafter, the support shaft 19 will be referred to also as the swing shaft 19.

The main enclosure 17*a* accommodates an essential section of a ball screw mechanism. In the present embodiment, the linear-motion output shaft 14*a* serves as the threaded shaft of the ball screw mechanism, a spiral thread groove 14*aa* being formed in the outer peripheral surface thereof. Further, the ball screw mechanism has cylindrical nut members 20 and 22 externally inserted coaxially to the linear-motion output shaft 14*a*. The nut members 20 and 22 are constructed such that the nut member main body 20 and the cylindrical member 22 are combined into one piece.

The nut member main body 20 is disposed in the main enclosure 17*a* such that the central portion thereof in the direction of the axial center is positioned between the swing shafts 19 and 19. More specifically, the nut member main body 20 is provided such that the axial center of the nut member main body 20 is orthogonal to the axial centers of the swing shafts 19 and 19 substantially at the center therein. The internal peripheral surface of the nut member main body 20 has a thread groove, and a plurality of balls 21 is retained in the internal peripheral surface of the nut member main body 20 and engaged with the thread groove 14*aa*. Rotating the nut members 20 and 22 about the axial center of the linear-motion output shaft 14*a* causes the balls 21 to roll along the thread groove 14*aa* while the linear-motion output shaft 14*a* moves in the direction of the axial center relative to the nut members 20 and 22.

The cylindrical member 22 is secured to one end of the nut member main body 20 in the direction of the axial center (the end adjacent to the subsidiary enclosure 17*b*) and externally inserted onto the linear-motion output shaft 14*a* coaxially with the nut member main body 20. The cylindrical member 22 has a clearance between itself and the linear-motion output shaft 14*a* and extends from the interior of the main enclosure 17*a* to the interior of the subsidiary enclosure 17*b*. The cylindrical member 22 is connected through a dog thereby to be secured to the nut member main body 20.

Further, bearings 23*a* and 23*b*, which are coaxial with the nut member main body 20, are interposed between the outer peripheral surface of the other end of the nut member main body 20 (the end on the opposite side from the subsidiary enclosure 17*b*) and the inner peripheral surface of the main enclosure 17*a* and between the outer peripheral surface of the nut member main body 20 of the cylindrical member 22 and the inner peripheral surface of the main enclosure 17*a*, respectively. Further, a bearing 23*c*, which is coaxial with the nut member main body 20, is interposed between the outer peripheral surface of the end of the cylindrical member 22 opposite from the nut member main body 20 and the inner peripheral surface of the subsidiary enclosure 17*b*. With this arrangement, the nut member main body 20 and the cylindrical member 22 are supported by the enclosure 17 through the intermediary of the bearings 23*a*, 23*b*, and 23*c* such that the nut member main body 20 and the cylindrical member 22 may integrally rotate about the axial centers thereof, i.e., about the axial center of the linear-motion output shaft 14*a*.

In the present embodiment, the nut member main body 20 and the cylindrical member 22 are separate structures. Alternatively, however, the nut member main body 20 and the cylindrical member 22 may be combined into one piece.

Here, when the nut members 20 and 22 rotate, the linear-motion output shaft 14*a* moves in the direction of the axial center thereof, causing a force in the direction of the axial center (thrust force) to act on the nut members 20 and 22. In the present embodiment, therefore, among the bearings 23*a*, 23*b*, and 23*c*, the bearings 23*a* and 23*b* positioned adjacently to the axial ends of the nut member main body 20 are constituted of angular bearings. In this case, a jaw 20*a* formed on the outer peripheral surface of the nut member main body 20 is abutted against an end surface adjacent to the bearing 23*b* out of both end surfaces in the axial direction of the inner ring of the bearing 23*a*. Further, an annular cap member 24 attached to an end of the main enclosure 17*a*, which end is opposite from the subsidiary enclosure 17*b*, is abutted against an end surface on the opposite side from the bearing 23*b* out of both end surfaces in the axial direction of the outer ring of the bearing 23*a*. Further, a jaw 22*a* formed on the outer peripheral surface of the cylindrical member 22 is abutted against an end surface adjacent to the bearing 23*a* out of both axial end surfaces of the inner ring of the bearing 23*b*. Further, a jaw 17*aa* formed on the inner peripheral surface of an end portion of the main enclosure 17*a*, which end portion is adjacent to the subsidiary enclosure 17*b*, is abutted against an end surface on the opposite side from the bearing 23*a* out of both axial end surfaces of the outer ring of the bearing 23*b*. With this arrangement, a thrust force which acts on the nut members 20 and 22 when the nut member main body 20 rotates is received by the main enclosure 17*a* through the intermediary of the bearings (angular bearings) 23*a* and 23*b*. In this case, the nut members 20 and 22 function as inner collars interposed between the inner rings of the bearings 23*a* and 23*b*.

A cylindrical outer collar 25 externally inserted onto the nut members 20 and 22 is interposed between the outer ring of the bearing 23*a* and the outer ring of the bearing 23*b*. The outer ring of the bearing 23*a* is placed between the outer collar 25 and the annular cap member 24, and the outer ring of the bearing 23*b* is placed between the outer collar 25 and the jaw 17*aa* of the main enclosure 17*a*.

The bearing members 18 and 18 for swingably supporting the enclosure 17 by the swing shafts 19 and 19 could alternatively be disposed outside the outer collar 25. This, however, would add to the width of the enclosure 17 in the direction of the axial centers of the swing shafts 19 and 19, i.e., the width in the lateral direction thereof, and also add to the widths of the upper link member 5 and the linear-motion actuator 14 in the lateral direction.

According to the present embodiment, therefore, the main enclosure 17*a* and the outer collar 25 inside thereof are provided with openings 17*ab* and 25*b* at the locations where the bearing members 18 are installed (the locations between the bearings 23*a* and 23*b*), as illustrated in FIG. 3. Thus, the bearing members 18 are attached to the main enclosure 17*a* such that the bearing members 18 are positioned within the openings 17*ab* and 25*b* and close to the outer peripheral surfaces of the nut members 20 and 22. More specifically, the opening 25*b* is formed in the cylindrical outer collar 25 by cutting off a part of the side wall thereof. Further, a side wall of the main enclosure 17*a* having the square-tubular shape also has the opening 17*ab* having approximately the same shape as the contour of the bearing member 18. The bearing member 18 is disposed within the openings 17*ab* and 25*b* and bolted to the main enclosure 17*a*. Thus, the width of the main enclosure 17*a* (the width of the swing shaft 19 in the direction of the axial center thereof) minimizes at the installation location of each of the bearing members 18 by restraining each of the bearing members 18 from projecting from the outer surface of the main enclosure 17*a*.

As illustrated in FIG. 4, a bracket 26 made integral with the subsidiary enclosure 17*b* is protrusively provided sideways (in the direction substantially orthogonal to the axial center of the linear-motion output shaft 14*a* and the axial center of the swing shaft 19) from the outer surface of the subsidiary enclosure 17*b*. In the present embodiment, the bracket 26 protrudes from the subsidiary enclosure 17*b* toward the guide rail 11 (see FIG. 2). A housing 16*b* of the electric motor 16 is secured to the bracket 26. In this case, an output shaft (rotating output shaft) 16*a* of the electric motor 16 is oriented in the directional parallel to the axial center of the linear-motion output shaft 14*a*, penetrating a hole 26*a* provided in the bracket 26. Thus, the electric motor 16 is disposed such that the inner end surface thereof is substantially flush with the inner end surface of the enclosure 17 at above the rear end portion of the linear-motion output shaft 14*a*, restraining the electric motor 16 from projecting outward in the lateral direction. Moreover, the electric motor 16 is closer to the guide rail 11, permitting a reduction in the inertial moment of the leg link 3 about the first joint 4, i.e., about the curvature center 4*a* of the guide rail 11.

The output shaft 16*a* of the electric motor 16 has a drive pulley 27*a* secured thereto, the drive pulley 27*a* being integrally rotational with the output shaft 16*a*. A side wall of the subsidiary enclosure 17*b* has a hole 17*ba* at a location opposing the drive pulley 27*a* in the direction orthogonal to the axial center of the linear-motion output shaft 14*a*. The drive pulley 27*a* opposes the cylindrical member 22 inside the subsidiary enclosure 17*b* through the hole 17*ba*.

The subsidiary enclosure 17*b* accommodates a driven pulley 27*b*, which is coaxial with the cylindrical member 22 and located between the bearings 23*b* and 23*c*. The driven pulley 27*b* is inserted in the outer peripheral surface of the cylindrical member 22 such that the driven pulley 27*b* can be rotated integrally with the nut members 20 and 22, and opposes the drive pulley 27*a* through the hole 17*ba*. An end surface of the driven pulley 27*b*, which end surface is adjacent to the bearing 23*c*, is abutted against an end surface of the inner ring of the bearing 23*c*. A cylindrical collar 28 externally inserted onto the cylindrical member 22 is interposed between an end surface of the driven pulley 27*b*, which end surface is adjacent to the bearing 23*b*, and the inner ring of the bearing 23*b*.

Further, a belt 27*c* is wound around the drive pulley 27*a* and the driven pulley 27*b*, and these two pulleys 27*a* and 27*b* rotate in an interlocking manner by the belt 27*c*. With this arrangement, a rotational driving force output through the output shaft 16*a* by the electric motor 16 is transferred to the cylindrical member 22 through the intermediary of a rotation transmitting mechanism (a pulley-belt rotation transmitting mechanism) constituted of the drive pulley 27*a*, the belt 27*c*, and the driven pulley 27*b*. In this case, the nut member main body 20 is rotationally driven integrally with the cylindrical member 22, and accordingly, the linear-motion output shaft 14*a* is driven to move in the direction of the axial center thereof. In other words, the rotational driving force of the electric motor 16 is converted into a translational force in the direction of the axial center of the linear-motion output shaft 14*a* through the pulley-belt rotation transmitting mechanism and the ball screw mechanism described above.

In the present embodiment, the electric motor 16 incorporates a speed reducer, which is not shown, and the rotational driving force generated in a rotor of the electric motor 16 is output from the output shaft 16*a* through the speed reducer.

As illustrated in FIG. 3 and FIG. 4, a stopper member 29 which restricts the movement amount of the linear-motion output shaft 14*a* is attached to an end of the linear-motion output shaft 14*a*, which end projects from the interior of the enclosure 17 toward the subsidiary enclosure 17*b* (hereinafter referred to as the rear end of the linear-motion output shaft 14*a*). The stopper member 29 is constructed of a nut 29*a* screwed to an external thread 14*ab* protruding from an end surface of the rear end of the linear-motion output shaft 14*a*, a metal washer 29*b* which is externally inserted onto the external thread 14*ab* and sandwiched between the end surface of the rear end of the linear-motion output shaft 14*a* and the nut 29*a*, and an annular cushioning member 29*c*. The annular cushioning member 29*c* is formed of an elastic material, such as urethane rubber, and interposed between the washer 29*b* and the nut 29*a*.

In this case, the outside diameter of the stopper member 29 is slightly larger than the outside diameter of the linear-motion output shaft 14*a* (more specifically, the maximum outside diameter of the portion which projects from the subsidiary enclosure 17*b*) such that the washer 29*b* of the stopper member 29 eventually abuts against the end surface of the cylindrical member 22 (the end surface on the opposite side from the nut member main body 20) when the linear-motion output shaft 14*a* moves in the direction for the stopper member 29 to approach the subsidiary enclosure 17*b* (toward the left in FIG. 3 and FIG. 4). This abutting restricts further movement of the linear-motion output shaft 14*a*. Further, the annular cushioning member 29*c* elastically deforms to reduce an impact at the time of the abutting. In addition, the washer 29*b* is disposed on the abutting side of the annular cushioning member 29*c* to prevent the annular cushioning member 29*c* from being stuck in the cylindrical member 22 or the like with a resultant malfunction. In the following description, the movement of the linear-motion output shaft 14*a* which causes the stopper member 29 to move toward the subsidiary enclosure 17*b* will be referred to as the forward movement of the linear-motion output shaft 14*a*, while the movement of the linear-motion output shaft 14*a* in the opposite direction therefrom will be referred to as the backward movement of the linear-motion output shaft 14*a*.

Here, when the stopper member 29 abuts against the end surface of the cylindrical member 22 in a state wherein the rotational driving force (the rotational driving force in the direction for the linear-motion output shaft 14*a* to move forward) from the electric motor 16 is acting on the cylindrical member 22, the rotational driving force is applied from the cylindrical member 22 to the stopper member 29. In this case, if the rotational driving force were the one in the direction for loosening the nut 29*a* of the stopper member 29 relative to the external thread 14*ab*, then toe nut 29*a* might loosen. For this reason, in the present embodiment, the rotational direction for tightening the nut 29*a* and the direction of rotation of the nut members 20 and 22 when the linear-motion output shaft 14*a* moves forward are set such that the direction of the rotational driving force applied from the cylindrical member 22 to the stopper member 29 when the forward movement of the linear-motion output shaft 14*a* causes the stopper member 29 to abut against the end surface of the cylindrical member 22 will be the direction for tightening the nut 29*a* of the stopper member 29. For example, in the case where the direction of the threading of the external thread 14*ab* and the nut 29*a* is set such that the nut 29*a* is tightened relative to the external thread 14*ab* by turning the nut 29*a* clockwise, the direction of threading of the linear-motion output shaft 14*a* and the nut members 20 and 22 is set such that the linear-motion output shaft 14*a* moves forward (the nut members 20 and 22 move backward relative to the linear-motion output shaft 14*a*) by turning the nut members 20 and 22 of the ball screw mechanism clockwise. This arrangement restrains the rotational driving force in the direction for loosening the nut 29*a* from acting on the stopper member 29 when the stopper 29 abuts against the end surface of the cylindrical member 22 due to the forward movement of the linear-motion output shaft 14*a*.

The above has described the detailed structure of the linear-motion actuator 14.

The motive power transferring mechanism 15 of each of the drive mechanisms 9 will be described with reference to FIG. 2.

The motive power transferring mechanism 15 has a crank arm 30, which is provided on the lower link member 7 coaxially with the joint axis of the third joint 8 (the axial center of the support shaft 8*a*), and a connecting rod 31 extending coaxially with the linear-motion output shaft 14*a* between the crank arm 30 and the linear-motion output shaft 14*a*. Of both ends of the connecting rod 31 in the lengthwise direction, one end adjacent to the linear-motion output shaft 14*a* is secured to the linear-motion output shaft 14*a* by screwing an external thread 31*a* protruding from an end surface of the connecting rod 31 (shown in FIG. 3 and FIG. 4) into the linear-motion output shaft 14*a* (refer to FIG. 3 and FIG. 4). The other end of the connecting rod 31 is swingably attached to a swing support portion 30*a* at an end of the crank arm 30. Although not illustrated in detail, the connecting rod 31 is swingably supported by the swing support portion 30*a* of the crank arm 30 via a spherical joint. A resin spring washer is interposed between the connecting rod 31 and the crank arm 30 to absorb a backlash of the spherical joint.

The above has described the details of the motive power transferring mechanism 15.

In the motive power transferring mechanism 15, when the electric motor 16 is operated to cause the linear-motion output shaft 14*a* of the linear-motion actuator 14 to generate a translational force in the direction of the axial center thereof, the generated translational force is applied to the swing support portion 30*a* of the crank arm 30 through the connecting rod 31. For example, a translational force F acts, as indicated by an arrow F in FIG. 2. At this time, the swing support portion 30*a* is decentered relative to the joint axis of the third joint 8, so that the translational force F acting on the swing support portion 30*a* (more specifically, a component of the translational force F, which component is in the direction orthogonal to the straight line connecting the joint axis of the third joint 8 (the axial center of the support shaft 8*a*) and the swing support portion 30*a*) causes a moment (torque) about the joint axis of the third joint 8 to act on the lower link member 7. This torque rotationally drives the lower link member 7 relative to the upper link member 5, bending or stretching the leg link 3 at the third joint 8. In this case, according to the present embodiment, the swing support portion 30*a* is disposed above the straight line connecting the joint axis of the third joint 8 (the axial center of the support shaft 8*a*) and the swing shaft 19, as observed in the axial direction of the joint axis of the third joint 8. Hence, the third joint 8 is driven in the direction in which the leg link 3 stretches by causing the linear-motion output shaft 14*a* of the linear-motion actuator 14 to generate a translational force in the backward movement direction (a translation force which provides a tensile force between the swing support portion 30*a* of the crank arm 30 and the nut members 20 and 22). In this case, the axial centers of the swing shafts 19 and 19 for swinging the enclosure 17 as the leg link 3 bends or stretches are orthogonal to the axial centers of the nut members 20 and 22 in the nut members 20 and 22 of the ball screw mechanism, thus making it possible to restrain, as much as possible, a bending force from acting on the linear-motion output shaft 14*a* inside the nut members 20 and 22. This allows the linear-motion output shaft 14*a* to stably and smoothly move in the axial direction as the nut members 20 and 22 are rotationally driven.

The above has described the major mechanical construction of the walking assistance device A according to the present embodiment. Although not illustrated, the walking assistance device A is provided with a controller including a microcomputer and the like and a power battery at appropriate locations therein in order to control the operation of the electric motor 16 of the linear-motion actuator 14. For example, the controller is installed inside the base frame 1*b* of the seating assembly 1, and the power battery is installed to the upper link member 5. Further, the walking assistance device A is provided with sensors for detecting tread forces of a user and sensors for detecting bending angles of the leg links 3, and outputs of these sensors are used to control the operation of the electric motor 16.

In the walking assistance device A, the third joint 8 of one of the leg links 3 which is in contact with the ground is driven such that, when the user walks, a load (upward translational force) for supporting a part of the weight of the user steadily acts on the user from the seating assembly 1. More specifically, a translational force of a predetermined value (e.g., a translational force for supporting a predetermined percentage (e.g., 20%) of the weight of the user) is defined as a target load to be applied from the seating assembly 1 to the user, and a torque of the third joint 8 (a torque in the direction in which the leg link 3 stretches) required to generate the target load is determined by arithmetic processing by a controller, which is not shown. Then, the output torque of the electric motor 16 is controlled such that the required torque acts on the third joint 8. Thus, the target load is applied from the seating assembly 1 to the user, thereby reducing the burden on the legs of the user.

In the embodiment described above, the load transmit section has been formed of the seating assembly 1 having the saddle-shaped seat 1*a*. Alternatively, however, the load transmit section may be formed of a harness-shaped flexible member to be attached around the waist of a user. The load transmit section preferably has a portion which comes in contact with the crotch of the user in order to apply an upward translational force to the body trunk of the user.

In the embodiment described above, the first joint 4 has the arcuate guide rail 11, which is set such that the curvature center 4*a* of the guide rail 11 serving as the longitudinal swing support point of each of the leg links 3 is positioned above the seating assembly 1. Alternatively, however, the first joint 4 may have a simple joint structure in which, for example, the upper end of the leg link 3 is rotatably supported by a shaft in the crosswise direction (the lateral direction) besides or below the seating assembly 1.

To assist the walking of a user having a problem with one leg due to bone fracture or the like, only one of the right and the left leg links 3 and 3 in the embodiment, whichever leg the user is having a problem with, may be used and the other leg link may be omitted.

What is claimed is:

1. A walking assistance device, comprising:

a load transmit assembly which transfers a load for supporting a part of the weight of a user to the body trunk of the user;

a foot-worn assembly to be attached to a foot of the user;

a leg link which connects the foot-worn assembly to the load transmit assembly, the leg link comprising an upper link member extended from the load transmit assembly via a first joint, a lower link member extended from the foot-worn assembly via a second joint, and a third joint which bendably connects the upper link member and the lower link member; and a drive mechanism for driving the third joint, wherein the drive mechanism has a linear-motion actuator including an electric motor mounted on the upper link member, a nut member which is rotationally driven by the electric motor and disposed in an enclosure swingably supported by the upper link member, and a linear-motion output shaft having a thread groove formed in an outer peripheral surface thereof, the thread groove screwing with the nut member through the intermediary of a ball retained in the nut member, and a crank arm which is secured to the lower link member coaxially with a joint axis of the third joint and swingably attached to one end of the linear-motion output shaft, and the drive mechanism is constructed such that a translational force output from the linear-motion output shaft of the linear-motion actuator is converted into a rotational driving force of the third joint through the crank arm.

2. The walking assistance device according to claim 1, wherein a pair of angular bearings which support the nut member by the enclosure such that the angular bearings are provided, being spaced apart in the direction of the axis line of the nut member, a pair of opposing openings having an axis line orthogonal to the axis line of the nut member is formed in an outer collar provided between outer rings of the angular bearings, and the bearing which is positioned in each opening and attached to the enclosure is rotatably supported by a support shaft protrusively provided on the upper link member.

3. The walking assistance device according to claim 2, wherein the load transmit assembly comprises a seating member on which a user sits astride, and the first joint comprises an arcuate guide rail, which is connected to the seating member, extends in a longitudinal direction and which has the center of curvature thereof at above the seating member, and a slider which is secured to an upper end of the upper link member and which movably engages the guide rail.

4. The walking assistance device according to claim 2, wherein an output shaft of the electric motor is provided in parallel to the axis line of the nut member.

5. The walking assistance device according to claim 2, wherein the nut member functions as an inner collar interposed between the inner rings of the pair of angular bearings.

6. The walking assistance device according to claim 1, wherein the load transmit assembly comprises a seating member on which a user sits astride, and the first joint comprises an arcuate guide rail, which is connected to the seating member, extends in a longitudinal direction, and which has the center of curvature thereof at above the seating member, and a slider which is secured to an upper end of the upper link member and which movably engages the guide rail.

7. The walking assistance device according to claim 1, wherein an output shaft of the electric motor is provided in parallel to the axis line of the nut member.

* * * * *